United States Patent
Hoyt

(10) Patent No.: US 6,566,143 B2
(45) Date of Patent: May 20, 2003

(54) MULTIPLE LABEL FLUORESCENCE POLARIZATION ASSAY SYSTEM AND METHOD

(75) Inventor: Clifford C. Hoyt, Needham, MA (US)

(73) Assignee: Cambridge Research & Instrumentation, Inc., Woburn, MA (US)

(*) Notice: Subject to any disclaimer, the term of this patent is extended or adjusted under 35 U.S.C. 154(b) by 0 days.

(21) Appl. No.: 09/794,903

(22) Filed: Feb. 26, 2001

(65) Prior Publication Data

US 2001/0033374 A1 Oct. 25, 2001

Related U.S. Application Data

(60) Provisional application No. 60/184,844, filed on Feb. 25, 2000.

(51) Int. Cl.[7] ............................................... G01N 21/76
(52) U.S. Cl. .................... 436/172; 356/317; 356/369; 250/459.1
(58) Field of Search .................. 356/317, 318, 356/416, 417, 418, 364, 365, 366, 368, 369, 370; 250/458.1, 459.1, 461.2; 436/172; 422/82.05, 82.08

(56) References Cited

U.S. PATENT DOCUMENTS

| | | | |
|---|---|---|---|
| 4,795,256 A | 1/1989 | Krause et al. | 356/320 |
| 5,834,203 A * | 11/1998 | Katzir et al. | 252/582 |
| 5,854,684 A | 12/1998 | Stabile et al. | 356/440 |
| 5,876,672 A * | 3/1999 | Dandliker et al. | 250/458.1 |
| 6,071,748 A | 6/2000 | Modlin et al. | 436/174 |
| 6,395,556 B1 * | 5/2002 | Lakowicz et al. | 422/82.07 |

FOREIGN PATENT DOCUMENTS

WO  WO 00/31518  6/2000

OTHER PUBLICATIONS

*Fluorescence Polarization and Anisotropy in High Through-put Screening: Perspectives and Primer*, John C. Owicki, Journal of Biomolecular Screening, vol. 5, No. 5, 2000, pp. 297–306.

International Search Report, dated May 22, 2001.

* cited by examiner

*Primary Examiner*—Cassandra Spyrou
*Assistant Examiner*—Arnel C. Lavarias
(74) *Attorney, Agent, or Firm*—Cohen, Pontani, Lieberman & Pavane

(57) ABSTRACT

A sample having a plurality of probe molecules is illuminated with at least one beam of excitation light that is linearly polarized along a first axis, thereby effecting fluorescence emission in a plurality of spectral bands. The intensity of a first component of fluorescence emission that is polarized along the first axis, as well as the intensity of a second component of fluorescence emission that is polarized along an orthogonal second axis, is measured for each of said plurality of spectral bands. These measurements are represented as a measurement vector M. Since each probe emits some limited amount of light in the characteristic band of another probe, this results in cross-talk between probes. The measurement vector is therefore corrected using an instrument response matrix A, which is generated by measuring the flux output of control samples which each have only a single probe species. A flux vector S is calculated according to $S = A^{-1}M$, and the fluorescence polarization FP is calculated from the S values.

1 Claim, 7 Drawing Sheets

MULTIPLE LABEL FLUORESCENCE POLARIZATION ASSAY SYSTEM AND METHOD

RELATED APPLICATIONS

This application claims priority from U.S. Provisional Patent Application Ser. No. 60/184,844 which was filed on Feb. 25, 2000.

BACKGROUND OF THE INVENTION

1. Field of the Invention

The invention is directed toward biochemical assays, more particularly toward assays using fluorescence polarization detection with two or more fluorescent labels in the experiment.

2. Description of the Related Art

Fluorescence polarization (FP) assays are becoming popular, since they are homogeneous and relatively safe, with no radioactive material. A good discussion is provided in the recent review article by John Owicki entitled "Fluorescence Polarization and Anisotropy in High Throughput Screening: Perspectives and Primer", published in the Journal of Biomolecular Screening, Volume 5, No. 5, pp 297–306 (2000).

The technique has at its core the detection of relative intensity of fluorescence emission in two orthogonal states of polarization. The labels are probe molecules (probes) which are excited with linearly polarized light and, depending on the molecular rotation rate and the excitation lifetime, their fluorescence emission is preferentially polarized along the axis of the excitation beam to a greater or lesser extent. If the molecular rotation time is long compared with the excited-state lifetime, the polarization of the emission is more highly polarized; if the rotation time is short, the emission is more nearly random in polarization. Since chemical binding or other reactions alter the molecular rotation time, they alter the FP value and so can be detected. FP is defined by the equation $$P = [I_{81} - I_{195}]/[I_{\parallel} + I_{\perp}] = [I_{81}/I_{\perp} - 1]/[I_{81}/I_{\perp} + 1] \quad [1]$$

where $I_{\parallel}$ and $I_{195}$ are the intensities of fluorescence emission polarized in the same sense as the polarization light and polarized orthogonal to it, respectively. There is a related concept termed fluorescence anisotropy (FA), which normalizes according to total fluorescence emission $I = I_{\parallel} + 2I_{\perp}$ and is defined by the equation $$r = [I_{\parallel} - I_{\perp}]/[I_{81} + 2I_{\perp}] = [I_{\parallel}/I_{\perp} - 1]/[I_{\parallel}/I_{\perp} + 2] \quad [2]$$

One can convert between P and r using the equations $$P = 3r/(2+r) \quad [3]$$

$$r = 2P/(3-P) \quad [4]$$

and in general, instrumentation or assays that provide a measurement of P will provide a measurement of r as shown in equations [3] and [4]; and vice versa. Similarly, instrumentation that provides an improved ability to measure one, will also provide an improved ability to measure the other. For simplicity, this specification refers to FP throughout, but is equally applicable to FA.

Measurements of FP are complicated by the presence of contaminant signals such as background fluorescence. These contribute fluorescence emissions with uncontrolled FP, shifting the measured FP. Optical filtering and other aspects of instrumental design are designed to minimize these signals. As reported by Owicki, post-processing by ratiometric corrections is a suitable way to correct these contaminants, since the contaminant is additive, rather than multiplicative, in nature.

There is at present no system or method for measuring an FP assay with multiple probes.

SUMMARY OF THE INVENTION

It is an object of the present invention to provide a system and method for performing multiple probe assays. It is another object to enable SNP (single nucleotide polymorphism) detection and coexpression using FP methods.

It is a further object of the invention is to measure the fluorescence polarization of two or more probes using the instrument described in my pending application Ser. No. 09/395,661 entitled "Fluorescence Polarization Assay System and Method", the contents of which are hereby incorporated by reference, together with suitable optical filters for the probes involved; and to attain the high accuracy and self-calibration feature described therein for multiple probes.

Yet another object of the invention is to provide a method for measuring the fluorescence polarization of two or more probes using instruments of the prior art such as the LJL Analyst or Acquest.

Another aim of the invention is to provide methods for measuring the fluorescence polarization of two or more probes at once with high accuracy, utilizing instruments of the type described in my pending co-filed application entitled "Instantaneous Dual Band Fluorescence Detection Systems", application Ser. No. 09/793853, the contents of which are hereby incorporated by reference.

It is also a goal of the present invention to provide for self-calibration that yields accurate values of FP without need for a priori knowledge of the target FP values of the probes.

The invention resides in a system and method for measuring FP or FA for two or more probes in a single sample, even though they may have overlapping excitation spectra or emission spectra, or both.

The probes can be simultaneously excited by a single source, if desired. The instrument provides apparatus to separate the fluorescence emission flux according to its spectral band and quantify it. For example, this can consist of a filter wheel containing filters that preferentially transmit emission flux from each probe in turn; or a birefringent network and a double-refraction element that spatially separates light according to its wavelength band and captures multiple bands instantaneously. Other arrangements can also be used to achieve the goal of quantifying the flux in various emission bands and polarization states.

Alternatively, the probes can be excited separately through use of sequential excitation at various wavelength bands in turn. The fluorescence emission flux and polarization state is measured for each type of excitation.

The equipment and method are analogous whether the probes are differentially excited through choice of excitation band; or emit differentially into various emission bands. For simplicity a common nomenclature is used; in either case, a given spectral band is said to correspond to a given probe, whether it is an excitation band used to preferentially excite that probe, or an emission band in which that probe preferentially emits.

To measure N probes, a total of at least 2N pieces of data, and preferably 4N pieces of data are required, comprising the various combinations of excitation polarization state, emission polarization state, and spectral band. These measurements are the raw data from which one will calculate the FP of each probe. However, if one were to take the values obtained at the spectral band corresponding to a given probe, and plug them into the FP equations of the prior art, one would not obtain the desired result, namely an accurate value of FP for that probe. hen 4N pieces of data are taken, the measurement can be inherently self-calibrating, with no need for a priori knowledge about the FP properties of the probes being measured. Or, one may take a single full data set comprising 4N pieces of data, from which an instrumental calibration is derived; subsequent readings taken with a smaller set of 2N pieces of data can be processed to yield accurately calibrated values of FP. The process for taking an initial full set of measurements, deriving an instrumental calibration, then working with subsequent smaller sets of measurements to yield absolutely calibrated readings of FP/FA, is described in my pending co-filed application entitled "Automatic G-Factor Calibration" application Ser. No. 09/793856, which is hereby incorporated by reference.

The present invention provides, among other things, a method for determining an accurate value of FP for each probe from the various raw data measurements, in a way that correctly accounts for the complex multi-probe assay system, the cross-talk between probes, and the physical limitations of the instrument.

One can speak of cross-talk between probes, meaning the degree to which a given probe is detected when the instrument is seeking to measure a different probe (the target probe). This occurs because the probes fluoresce over broad wavelength ranges which overlap, even when they fluoresce most intensely in mutually exclusive ranges.

Mathematically, we write the instrument's response to probe k when set to read probe j as $a_{jk}$, and one can write the instrumental response function for all probes and instrumental settings as a matrix A populated with elements $a_{jk}$. In such a matrix, the diagonal represents the response of the instrument to the target probes, while off-diagonal members represent cross-talk. For this reason, the A matrix is also called the cross-talk matrix for the probes and instrument involved. For two probes and two corresponding wavebands, this is a 2×2 matrix, and the cross-talk is represented by the second diagonal. The degree of isolation between flux from the different probes is never perfect due to instrumental limitations. In the usual case where probes have partially overlapping spectra the separation is fundamentally limited by the spectral cross-talk between the probes.

The core of the invention is the quantification of FP for multiple probes through measurement of the cross-talk by means of the instrumental response matrix A, or an equivalent formalism, and the use of this cross-talk information to determine the contribution of each probe to the measured flux readings in each spectral band and polarization state. From these derived quantities, termed the probe contributions, one can accurately calculate the FP or FA for each of the probes.

The matrix A can be measured using control samples that contain only a single probe each. Indeed it is possible to characterize a set of four matrices $\{a_{hh}, A_{hv}, A_{vh}, A_{vv}\}$ for all possible excitation and emission polarization states, when the instrumental response is known to vary as a function of polarization. This can be caused by factors such as polarization-dependent transmission in dichroic mirror elements, which shifts the spectral response and thus alters the contents of matrix A. The set of matrices may then be used to derive accurate values of the probe contributions, and thus of FP, despite polarization-dependent cross-talk in the overall assay.

It is possible to use the invention to measure and correct for the relative exposure times or lamp fluctuations associated with each measurement in the raw data set, if desired. Through these aspects of the invention and others described in more detail below, a multiple-probe FP is achieved, with accurate quantification of FP for each probe despite spectral cross-talk, instrumental polarization sensitivities, and fluctuations in exposure or lamp brightness.

The various features of novelty which characterize the invention are pointed out with particularity in the claims annexed to and forming a part of the disclosure. For a better understanding of the invention, its operating advantages, and specific objects attained by its use, reference should be had to the drawings and descriptive matter in which there are illustrated and described preferred embodiments of the invention.

BRIEF DESCRIPTION OF THE DRAWINGS

In the drawings.

The following figures are all intended to be schematic in nature, and like elements are denoted by the same number.

DETAILED DESCRIPTION OF THE PRESENTLY PREFERRED EMBODIMENTS

Throughout this discussion, the instrument and method are described for two labels, but the principle can be extended to three or more labels using the same methodology. Also, where analysis and algorithms are presented in the form of particular algebraic equations or matrices, this is purely for the purpose of explaining the invention; one may use other equations or algorithms that achieve the same end in order to practice the invention.

Throughout the following, one state of polarization is termed h and its complement is v. These need not be horizontal and vertical, but either h or v must correspond to the major axis of the state of polarization used to excite the sample in any given measurement.

Figure 1:
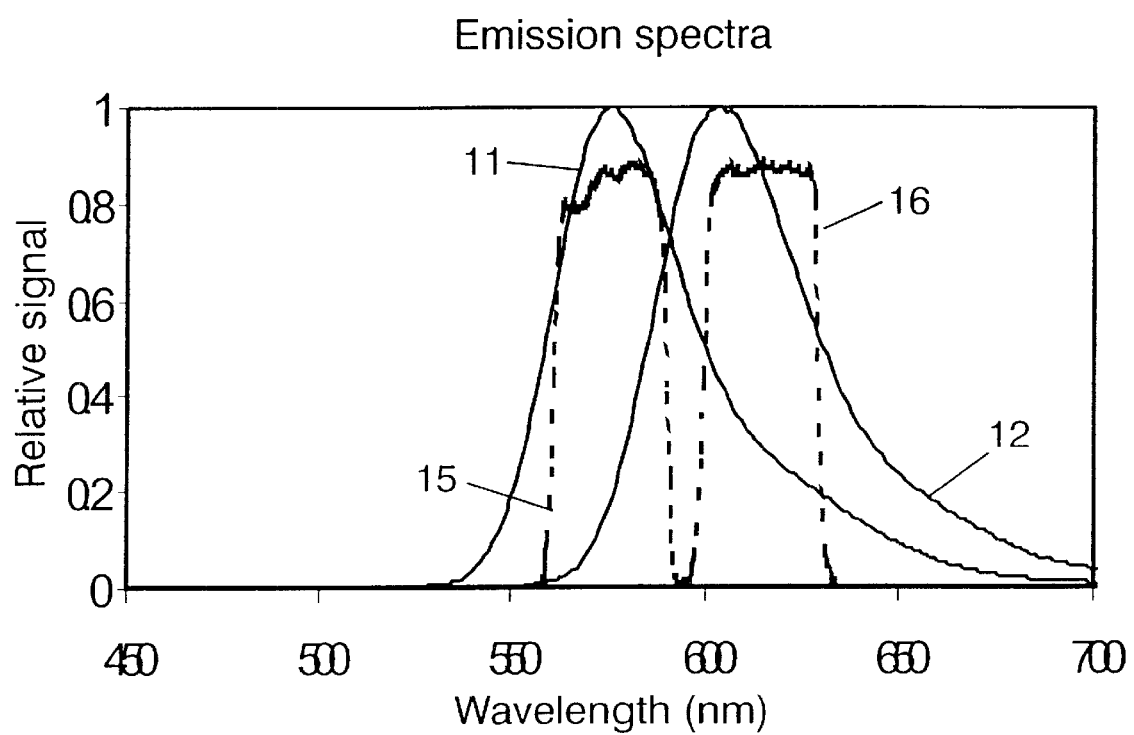
FIG. 1 shows the emission spectra of two probes together with the instrumental bands used to detect them.

FIG. 1 shows the emission spectra 11 and 12 of two probes whose fluorescent emissions are measured after passing through bandpass filters having respective transmission bands 15 and 16. These are chosen so that band 15 includes spectra 11, and band 16 includes spectra 12.

Figure 2:
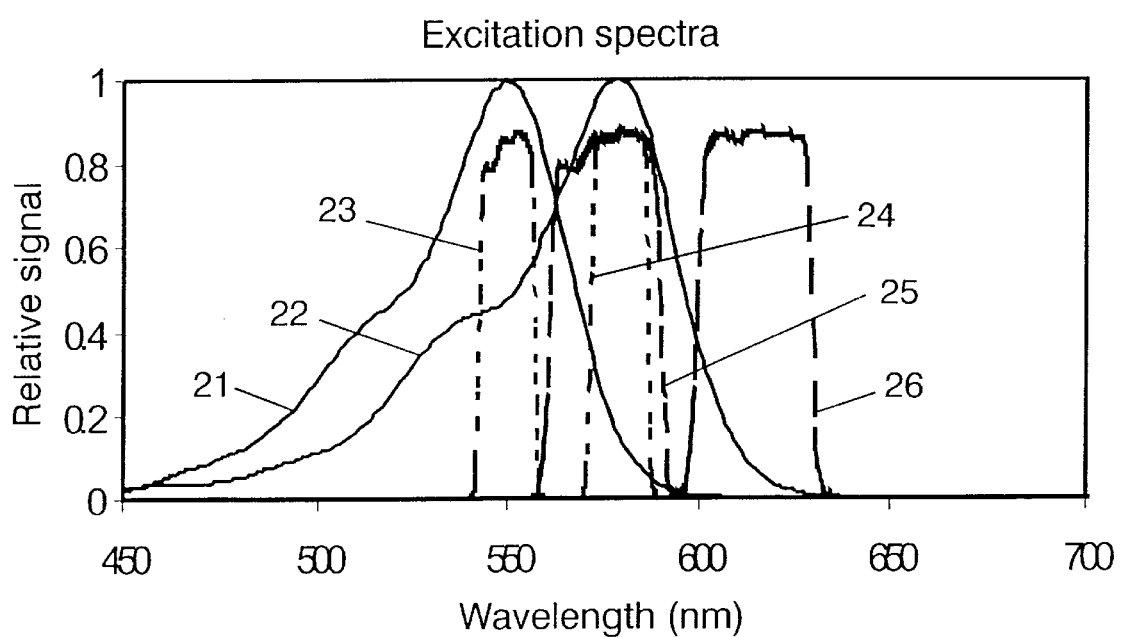
FIG. 2 shows the excitation spectra of two probes together with the excitation bands used to excite them.

FIG. 2 shows the excitation spectra 21 and 22 of two probes which are excited by sources whose wavelengths fall within excitation bands 23 and 24; and whose fluorescent emissions are measured after passing through bandpass filters having respective transmission bands 25 and 26. These are chosen so that emission flux in band 25 preferentially corresponds to excitation spectra 21 within band 23, and so that emission flux in band 26 preferentially corresponds to excitation spectra 22 within band 24.

In general one may use emission filters alone, or a combination of excitation sources and emission filters, to provide two sets of measurements at a detector. One set corresponds principally to the first probe, albeit with some contribution from the second probe; and the second corresponds principally to the second probe, albeit with some contribution from the first probe.

These measurements are undertaken for various combinations of excitation and emission polarization states, to obtain the data from which FP is calculated. If we denote a given measurement in terms of the excitation polarization, the emission polarization, and the spectral band selection as $m_{xeb}$, a two-probe measurement requires that one acquire e.g. the set $\{m_{vv1}, m_{vh1}, m_{vv2}, m_{vh2}\}$, $\{m_{hv1}, m_{hh1}, m_{hv2}, m_{hh2}\}$ $\{m_{vv1}, m_{hv1}, m_{vv2}, m_{hv2}\}$ or the set $\{m_{hh1}, m_{vh1}, m_{hh2}, m_{vh2}\}$. Note that the third subscript on m indicates the spectral band b, not the target probe p.

One can model the reading $m_{xeb}$ as $$m_{xeb} = F \cdot (S_{xe1} \cdot a_{xeb1} + S_{xe2} \cdot a_{xeb2}) \quad [5]$$

where:
- $a_{xejk}$ is the instrumental responsivity in band j to flux from probe k for excitation polarization x and emission polarization e;
- F is an exposure correction factor which reflects the relative amount of excitation flux for (and integration time, if the measurement is an integrating type), for that measurement compared to a nominal value;
- $S_{xep}$ indicates the flux produced under the nominal excitation flux, in excitation polarization state x into emission polarization state e, by sample probe p.

Fundamentally, one wishes to determine $s_{xep}$ from the measurements $m_{xeb}$. As equation [5] shows, the reading m obtained in a given band is the sum of signals from the probe p primarily associated with band b, along with signals from the other probe(s), weighted according to coefficients $a_{xejk}$. As noted earlier, one may write the coefficients $a_{jk}$ for a given choice of excitation state x and emission state e, as a two-dimensional matrix A with members $a_{jk}$.

Similarly, one may write the measurements as a vector M with members $m_b$ and the flux as vector S with members $s_p$.

By inverting A, one can calculate the value of $s_{xep}$ from the associated $m_{xeb}$ as $$S = A^{-1} M \quad [6]$$

provided that the measurements share the same exposure correction factor F.

This process can be done for any and all combinations of excitation and emission polarization states, yielding a set of vectors $S_{xe}$ from which one may calculate FP for probe p as $$FP_p = (s_{vvp} - s_{hvp})/(s_{vvp} + s_{hvp}) \quad [7a]$$

or equivalently $$FP_p = (s_{vvp} - s_{hvp})/(S_{hvp} + s_{vhp}) \quad [7b]$$

$$FP_p = (s_{hhp} - s_{vhp})/(S_{hhp} + s_{vhp}) \quad [7d]$$

So, neglecting for a moment any corrections for variations in exposure, one may obtain values for multi-probe FP/FA assays as follows:

1) obtain values for instrumental response matrix A for a given set of excitation and emission states, using control samples, as described in more detail below;
2) repeat step 1) for all combinations of excitation and emission states used, storing the various matrices as $\{A_{xe}, \ldots\}$, and inverting to yield $\{A^{-1}_{xe}, \ldots\}$
3) obtain values of the measurement vector M for the sample, for each combination of excitation and emission states used;
4) calculate the flux vector S from equation [6] for each combination of excitation and emission states used;
5) calculate FP from the S values according to equation [7a], [7b], [7c], or [7d].

To obtain the values of A, one may take measurements of control samples which have only a single probe species. From measurements of the same sample in each of the spectral bands, one obtains $a_{xebp}$ for all bands; i.e. one obtains a column of A for that set of excitation and emission states. By repeating for samples that have single pure species of each probe, one obtains all columns in A. This normalizes the analysis so unit values of S correspond to the fluxes produced by the control samples.

One can virtually eliminate the effect of exposure fluctuations F, or other random sources of error, in estimating A, by repeating this measurement several times. This is readily achieved, since the determination of A is undertaken once for a given combination of probes on a given instrument.

Figure 3:
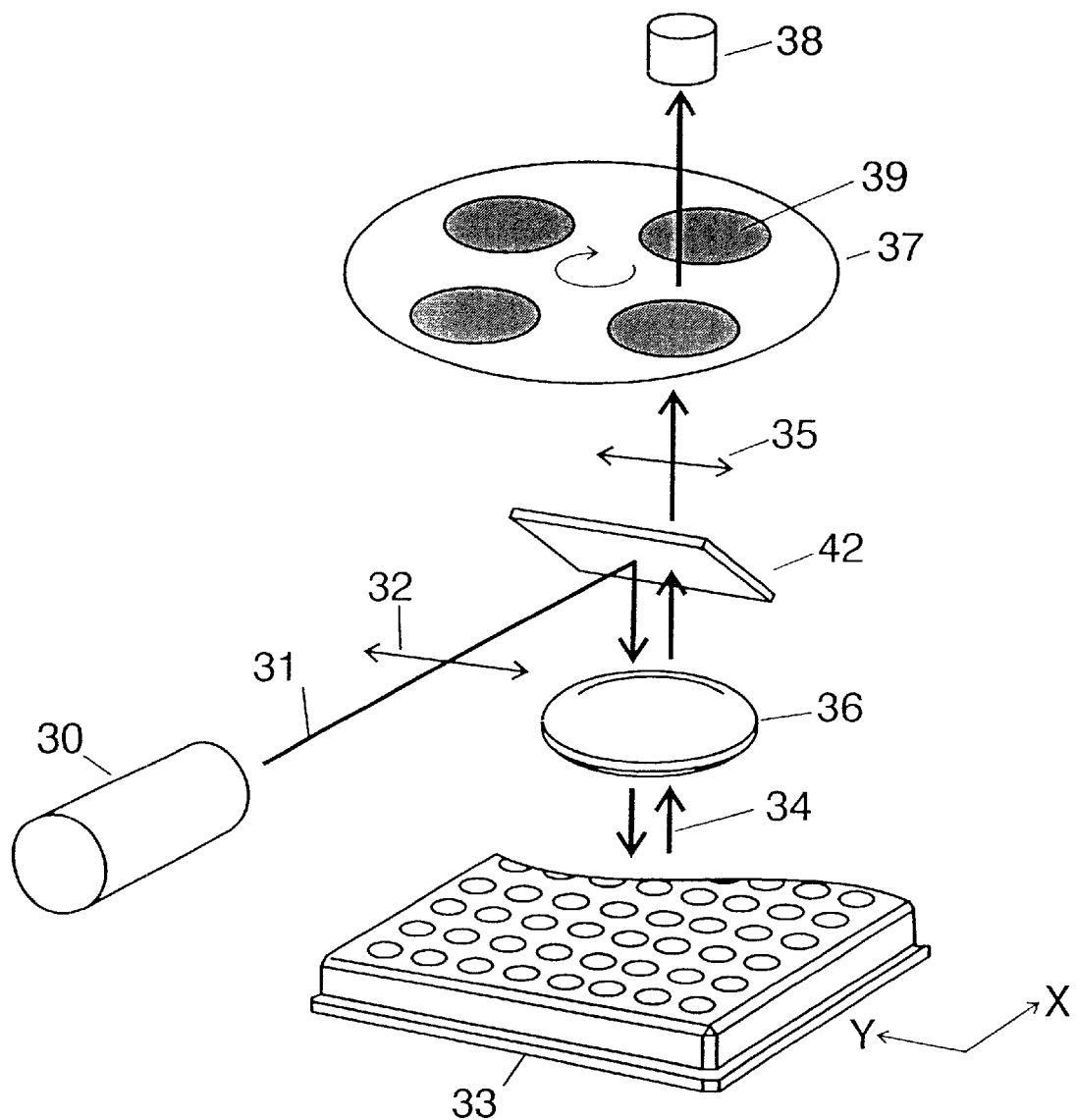
FIG. 3 shows a generalized diagram of a multiprobe FP instrument for use with multiple probes sharing a single excitation source.
Figure 4:
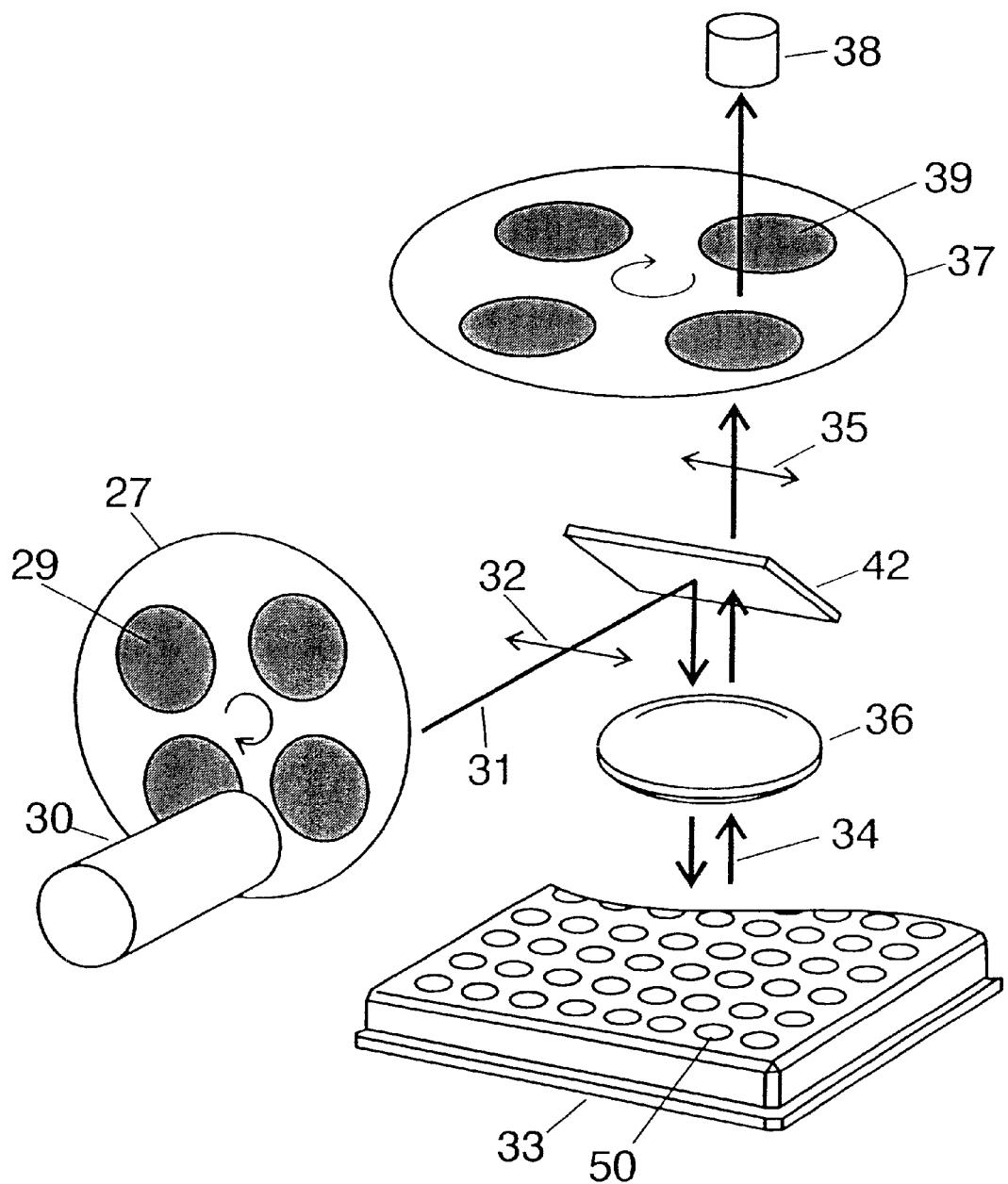
FIG. 4 shows a generalized diagram of a multi-probe FP instrument for use with multiple probes having multiple excitation sources.

The approach described in steps 1)–5) is suitable for use with any FP instrument, as shown in generalized form in FIG. 3 for a single-excitation system, or FIG. 4 for a system with excitation sources at multiple wavelengths, for example by providing a spectral selective element 27 having bandpass filters 29. Both instruments provide an excitation source 30 of light 31 having a chosen polarization state indicated by 32, which is reflected by dichroic mirror 42 and excites a sample 50 on microtiter plate 33 to emit fluorescent light 34. The microtiter plate 33 has an array of wells with samples being analyzed one at time; the plate is moved by an X–Y table or the like to permit analysis of all sample wells sequentially. The emission light 34 is captured by optics 36 and (having a longer wavelength than the excitation light 31) is transmitted by the dichroic mirror 42 and directed through one of bandpass filters 39 in spectral selective element 37 to a detector 38. The emission light 34 is shown as having state of polarization 35, which corresponds to the polarization state 32 of the emission light 31, and indicates molecular interaction with the label. The degree of polarization of the emitted light is a function of the molecular interaction; randomly polarized emission light would indicate no interaction.

This approach is suitable for use with hardware of the prior art, such as the LJL Analyst (Molecular Devices, Calif.) or other instruments that obtain measurements of a single excitation state, single emission state, and single spectral band, at a time. For such an instrument, a minimum of four exposures are required, one for each $m_{xeb}$ value.

It is possible to compensate for random fluctuations in exposure in such an instrument by noting the intensity of the excitation source via a reference detector that samples the excitation beam, and dividing the measurements $m_{xeb}$ by the relative intensity measure thus obtained.

The use of this technique has been shown for the case of a single excitation band for several emission bands, and this has certain practical benefits in terms of measurement simplicity. However, it is possible to perform the same measurement using multiple excitation bands, each with its own distinct emission band; or a hybrid, where several probes share a common excitation band while using distinct emission bands for measurement, and another probe(s) has a distinct excitation band. The formalism is identical to that described above, and is contemplated within the present invention. The key to the present invention is the use of the matrix A to correct for the instrumental cross-talk between bands, which can occur whether the probes are excited at a shared band or at multiple bands. However, if the probes are so widely separated in their spectral response for excitation and emission, and have such a small degree of cross-talk that there is no need for the matrix A, then there is no benefit to employing the cross-talk compensation of the present invention.

Figure 5:
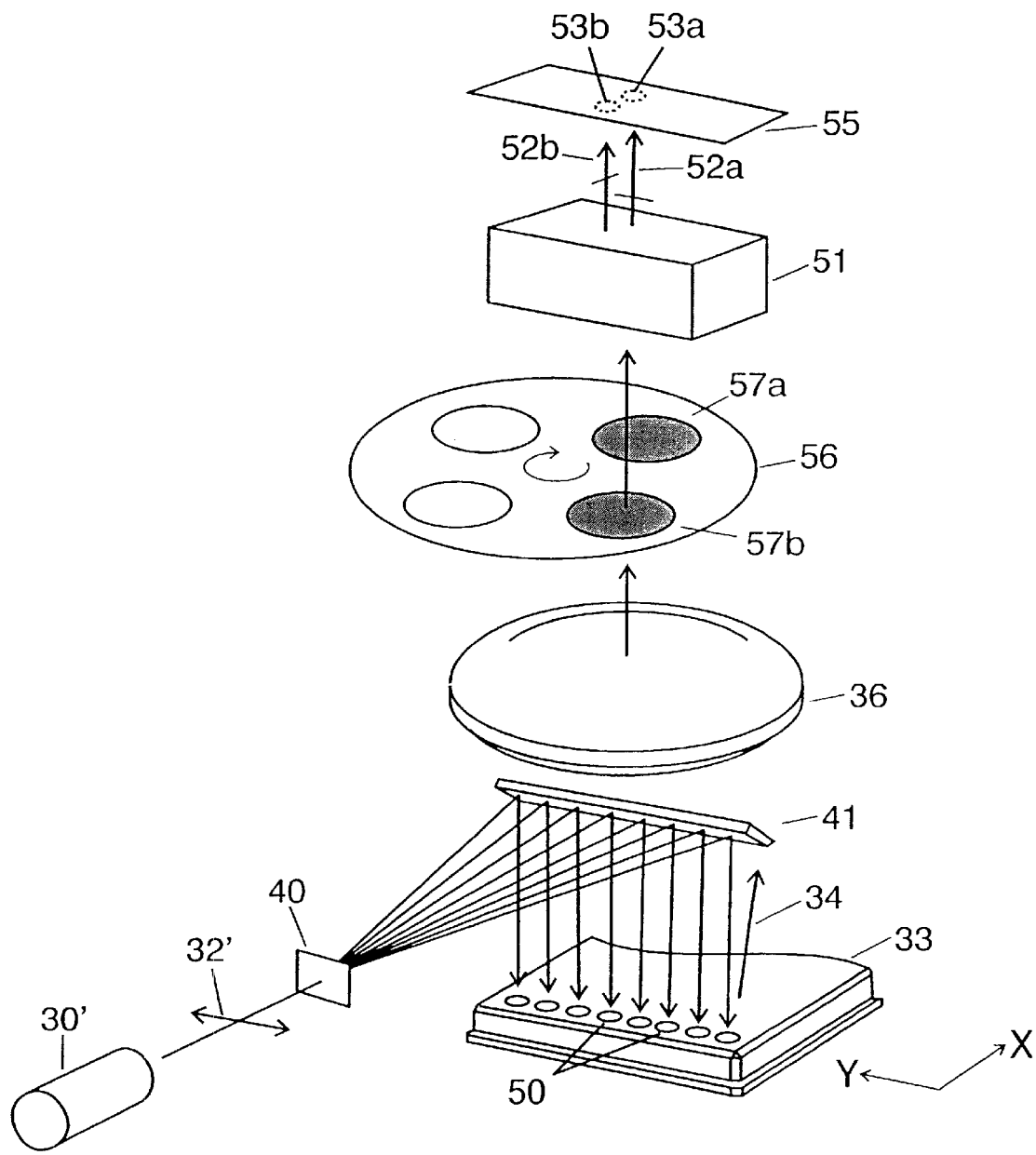
FIG. 5 shows a multi-probe FP instrument which measures emission flux in both states of polarization simultaneously, for a single band.

Other embodiments may be preferred when high assay speed or maximum precision are required. FIG. 5 shows an instrument used in a preferred embodiment of the invention, based on the design from my pending patent application Ser. No. 09/395,661. Its excitation source 30' provides light in polarization state 32' which is divided into substantially equal energy output beams by a diffractive beam splitter 40. The output beams are reflected by a mirror 41 to sample wells 50 at microtiter plate 33, producing fluorescent light 34. The mirror must be long enough to reflect all of the output beams, but narrow enough that it does not greatly occlude the optics 36. This light passes through optics 36 to a doubly-refractive element 51 that spatially separates light of h and v polarization states 52a and 52b, and directs them to distinct regions 53a and 53b on an imaging detector 55 (there are two detection regions for each sample 50). Filter wheel 56 contains filters 57a and 57b that spectrally select one band at a time, so that different wavelength bands of emitted light must be measured sequentially. This instrument enables simultaneous measurement of emission flux levels in the two orthogonal states of polarization.

Figure 6:
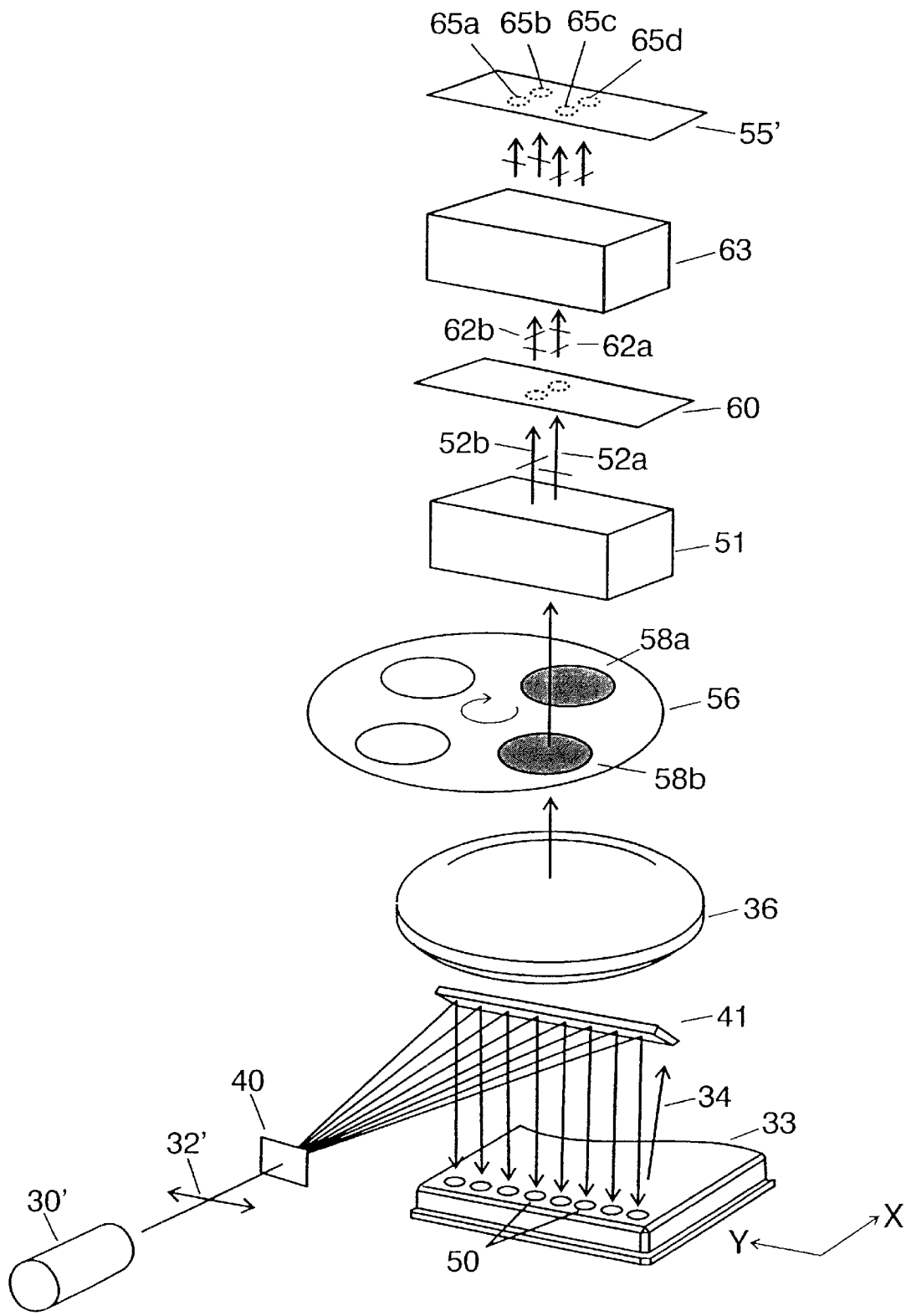
FIG. 6 shows a multi-probe FP instrument which measures emission flux in both states of polarization, in two bands, simultaneously.

Another preferred embodiment uses the instrument shown in FIG. 6. This instrument uses a design that is described more fully in my co-filed application "Instantaneous Dual Band Fluorescence Detection Systems", application Ser. No. 09/793853. This instrument comprises an excitation source 30' which provides a beam of light which is split into a plurality of output beams by a diffractive beam splitter 40, which beams in polarization state 32' illuminate samples 50 at plate 33, yielding fluorescent light 34. For reasons of clarity only one of these beams is shown, but there are as many emission beams 34 as there are output beams and sample wells being analyzed at a given time. Each beam passes through optics 36 and a selected one of the filters 58a, 58b . . . of the filter wheel 56. These are dual bandpass filters which transmit light in two spectral bands being analyzed; alternatively they may have a single wide passband which transmits both spectral bands. Double-refractive element 51 spatially separates light of h and v polarization states 52a and 52b, so they are offset in the x dimension from one another. These separated beams, which each carry both spectral bands, then encounter a birefringent network 60 that transforms the polarization of light to its complement for certain spectral bands, while leaving the polarization of light in the remaining spectral bands unaltered. In the present case the polarization state of one of the spectral bands is rotated, so that each of the emerging beams carries two spectral bands in two respective polarization states. For example, the beam 62a carries the first spectral band in the first polarization state and the second spectral band in the second polarization state, while the beam 62b carries the first spectral band in the second polarization state and the second spectral band in the first polarization state. The emission light next encounters a second double-refractive element 63 that spatially separates light of h and v polarization states in each of beams 62a and 62b in the y dimension. Because the light is initially split by element 51 into two spots according to polarization, and each of these has its polarization modified by network 60 and then is further split by element 63, the result is that four spots 65a–65d are produced at imaging detector 55'. These enable the simultaneous measurement of both emission states of polarization, in both spectral bands, for a given excitation state of polarization. Thus it is especially well-suited to assays which use a single excitation source and two probes having different but perhaps overlapping emission spectra.

These instruments are especially well-suited to use in multi-probe FP assays. First, these designs eliminate all tilted dichroic coatings, which introduce a polarization-dependent spectral signature. Thus, the instrumental responsivity matrix A is nearly independent of the excitation or emission state of polarization, and a single matrix A may be used instead of four matrices spanning each possible combination. Second, these instruments provide simultaneous measurement of both emission states of polarization, in either one band (as in FIG. 5) or in two bands (as in FIG. 6), so one can obtain excellent signal to noise by utilizing the so-called symmetric equations disclosed in my co-pending patent application Ser. No. 09/395,661, and can thus obtain absolutely calibrated values of FP. The latter embodiment provides quartets of measurements $m_{xeb}$ taken under identical exposure conditions, eliminating exposure fluctuation errors completely as a source of noise in the measurement.

Techniques and algorithms for taking advantage of these aspects are shown now. Cross-talk compensation can be incorporated into the symmetric equation of FP, as:

$$FP_1 = [a^{-1}_{11} \cdot (m_{hh1} - m_{hv1} + m_{vv1} + m_{vh1}) + a^{-1}_{12}$$

$$(m_{hh2} - m_{hv2} - m_{vv2} - m_{vh2})]/[$$

$$a_{-111}(m_{hh1} + m_{hv1} + m_{vv1}$$

$$+ m_{vh1})] \quad [8a]$$

$$FP_2 = [a^{-1}_{22} \cdot (m_{hh2}$$

$$- m_{hv2} + m_{vv2} - m_{vh2}) +$$

$$a^{-1}_{21}(m_{hh1} - m_{hv1}$$

$$+ m_{vv1} - m_{vh1})]/[a^{-1}_{22}$$

$$\cdot (m_{hh2} + m_{hv2} + m_{vv2} + m_{vh2})$$

$+a^{-1}{}_{21} \cdot (m_{hh1} + m_{hv1})$ $+m_{vv1} + m_{hv1})]$ [8a]

where $a^{-1}$ are the elements of the matrix $A^{-1}$, the matrix inverse of instrumental response matrix A. This gives an inherently self-calibrating measurement of FP for probes 1 and 2, as it is based on the symmetric equation of FP.

To compensate for exposure fluctuations, one calculates factors $\gamma_1 = [(m_{hh1} \cdot m_{hv1})/(m_{vv1}$ $\cdot m_{vh1})]^{1/2}$ [9a]

$\gamma_2 = [(m_{hh2} \cdot m_{hv2})/(m_{vv2}$ $\cdot m_{vh2})]^{1/2}$ [9b]

and then calculates FP ratios using equations $FP_1 = [a^{-1}{}_{11} \cdot (m_{hh1}$ $- m_{hv1} + \gamma_1 (m_{vv1} - m_{vh1}))$ $+ a^{-1}{}_{12} (m_{hh2} - m_{vh2} + m_{vv2} - m_{vh2})]/[a^{-1}{}_{11}$ $\cdot (m_{hh1} + m_{hv1} + \gamma_1$ $(m_{vv2} + m_{vh1})) + a^{-1}{}_{12}$ $\cdot (m_{hh2} + m_{hv2} + m_{vv2}$ $+ m_{vh2})]$ [10a]

$FP_2 = [a^{-1}{}_{22} \cdot (m_{hh2} - m_{hv2} + \gamma_2 (m_{vv2} - m_{vh2})) +$ $-{}^{1}{}_{21} \cdot (m_{hh1} - m_{hv1}$ $+ m_{vv1} - m_{vh1})]/[a^{-1}{}_{22}$ $\cdot (m_{hh2} + m_{hv2} + \gamma_2$ $(m_{vv2} m_{vh2})) + a^{-1}{}_{21}$ $\cdot (m_{hh1} + m_{hv1} m_{vv1}$ $+ m_{vh1})]$ [10b]

In the case where the instrument uses the design of FIG. 6, both spectral bands are acquired at once, and exposure correction factors $\gamma_1$ and $\gamma_2$ are necessarily the same. Then perfect exposure compensation is achievable using the equations $FP_1 = [a^{-1}{}_{11} (m_{hh1} - m_{hv1}$ $+ \gamma (m_{vv1} - m_{vh1})) + a^{-1}{}_{12}$ $(m_{hh2} - m_{hv2} + \gamma (m_{vv2}$ $- m_{vh2}))]/[a^{-1}{}_{11}$ $(m_{hh1} + m_{hv1} + \gamma (m_{vv1}$ $+ m_{vh1})) + a^{-1}{}_{12} (m_{hh2}$ $+ m_{hv2} + \gamma (m_{vv2}$ $+ m_{vh2}))]$ [11b]

$FP_2 = [a^{-1}{}_{22} (m_{hh2} - m_{hv2}$ $+ \gamma (m_{vv2} - m_{vh2})) + a^{-1}{}_{21}$ $(m_{hh1} - m_{hv1} + \gamma (m_{vv1}$ $- m_{vh1}))]/[a^{-1}{}_{22} (m_{hh2}$ $+ m_{hv2} + \gamma (m_{vv2} + m_{vh2})) +$ $a^{-1}{}_{21} (m_{hh1} + m_{hv1} +$ $\gamma (m_{vv1} + m_{vh1}))]$ [11b]

where $\gamma \equiv \gamma_1 = \gamma_2$.

Figure 7:
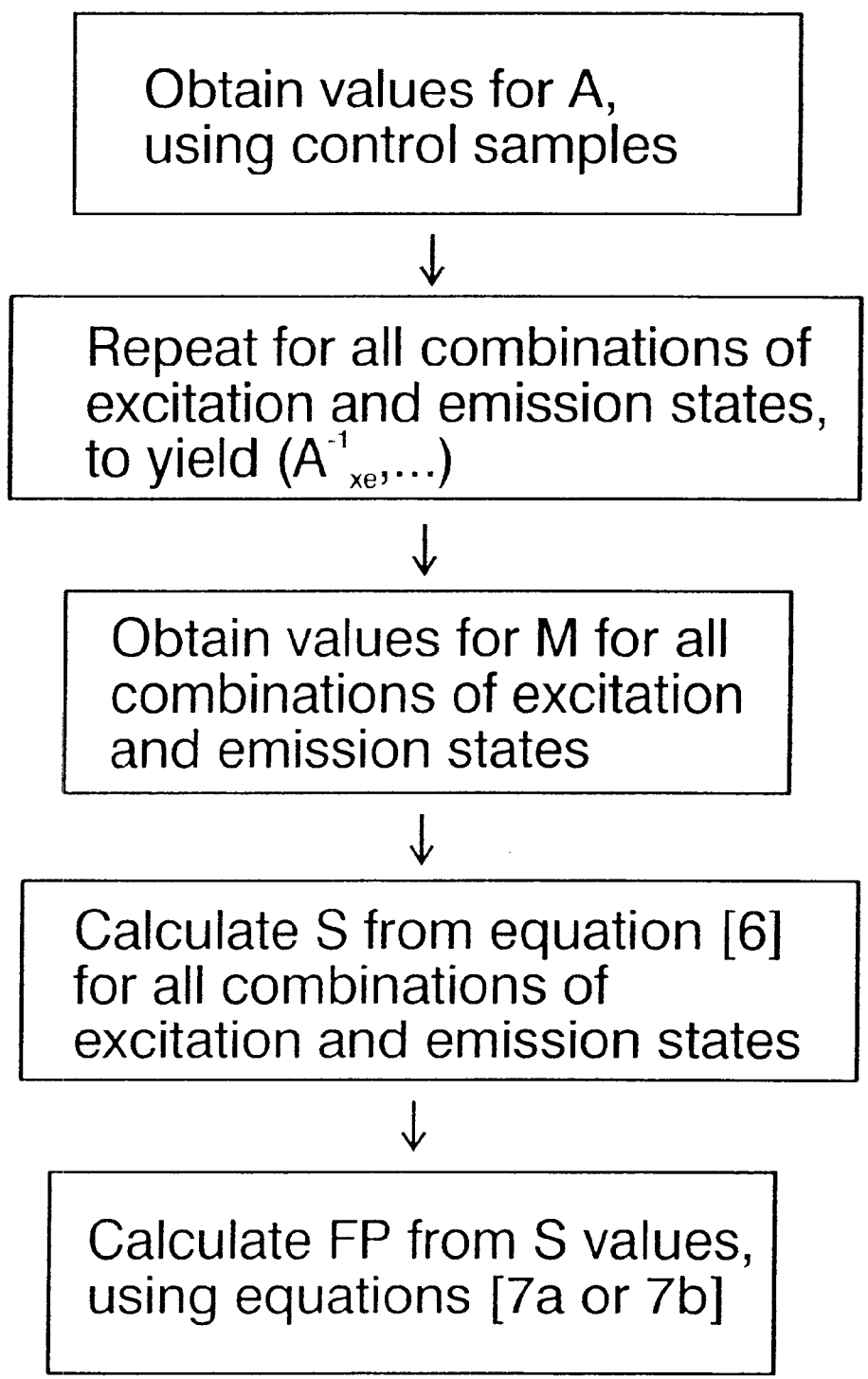
FIG. 7 shows a flow chart indicating how one derives the matrix A, and how to calculate the desired FP from the measured intensity in each spectral band and at each polarization setting.

With these instruments, one follows the procedure of FIG. 7, but uses the equations [8a–b], [10a–b], or [11a–b] to calculate the FP for each probe. Measurement of the A matrix is simplified with the apparatus of FIG. 6, since all matrix elements are measured with identical exposure times, reducing errors in that step.

The principles of this invention may be utilized with the teachings in my co-pending applications incorporated herein, as described above and in other ways that will be evident to those skilled in the arts of instrument design and polarized light. Similarly, use of optical elements or algorithms that achieve substantially the same results as the examples and embodiments shown here, may be undertaken with success, and the choice to do so will be dictated by engineering consideration, including such factors such as economy, size, ease-of-integration, computation speed, simplicity, and the like.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

I claim:

1. A method for measuring the fluorescence polarization of a plurality of probes in a single sample, which method compensates for spectral cross-talk among said plurality of probes, said method comprising illuminating a sample having a plurality of probes with at least one linearly polarized beam of excitation light, thereby effecting fluorescence emission in a plurality of spectral bands, measuring the intensity of a first component of fluorescence emission that is linearly polarized along a first axis, in each of said plurality of spectral bands, measuring the intensity of a second component of fluorescence emission that is linearly polarized along a second axis that is orthogonal to the first axis, in each of said plurality of spectral bands, illuminating each of a plurality of samples which each have only a respective one of said probes with at least one linearly polarized beams of excitation light, thereby effecting fluorescence emission in at least one of said plurality of spectral bands from each of said plurality of samples, measuring the intensities of said first and second components of fluorescence emission in each of said plurality of spectral bands for each of said samples which each have only a respective one of said probes, and compensating for spectral cross-talk amongst said plurality of probes by determining the relative contributions from each of said probes to the measured intensities of said first and second components of fluorescence emission at each spectral band, and calculating the fluorescence polarization of each of said plurality of probes based on said relative contributions.

* * * * *